United States Patent [19]

Floyd et al.

[11] Patent Number: 4,752,613
[45] Date of Patent: Jun. 21, 1988

[54] SULPHONAMIDOTHIENYLCARBOXYLIC ACID COMPOUNDS

[75] Inventors: David M. Floyd, Pennington; Philip D. Stein, Hopewell, both of N.J.

[73] Assignee: E. R. Squibb & Sons, Inc., Princeton, N.J.

[21] Appl. No.: 80,735

[22] Filed: Aug. 3, 1987

[51] Int. Cl.$^4$ .................. A61K 31/38; C07D 333/38
[52] U.S. Cl. .................................. 514/438; 514/381; 514/448; 549/71; 549/72; 549/77; 548/252
[58] Field of Search ........................... 549/71, 72, 77; 548/252; 514/438, 448, 381

[56] References Cited

U.S. PATENT DOCUMENTS 4,258,058  3/1981  Witte et al. .
4,443,477  4/1984  Witte et al. .

FOREIGN PATENT DOCUMENTS 194548A  3/1986  European Pat. Off. .

Primary Examiner—Alan Siegel
Attorney, Agent, or Firm—Lawrence S. Levinson; Stephen Venetianer

[57] ABSTRACT

Compounds represented by the formula

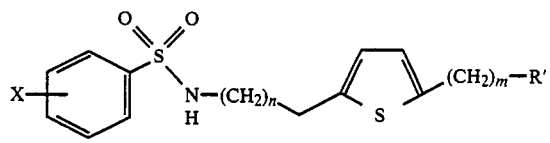

wherein X is halogen, lower alkyl, arylalkyl, alkoxy or hydroxy; wherein the phenyl ring is mono or disubstituted, R' is —COOH or

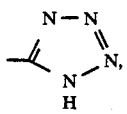

or

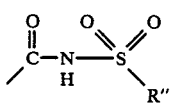

wherein R'' is lower alkyl or aryl and n and m are independently zero, one, two or three which are potent thromboxane $A_2$ receptor antagonists.

14 Claims, No Drawings

SULPHONAMIDOTHIENYLCARBOXYLIC ACID COMPOUNDS

FIELD OF THE INVENTION

The present invention relates to new sulphonamidothienylcarboxylic acid compounds. These novel compounds are useful as thromboxane receptor antagonists.

BACKGROUND OF THE INVENTION

U.S. Pat. No. 4,443,477 discloses sulphonamidophenylcarboxylic acid compounds which inhibit thrombocyte aggregation. U.S. Pat. No. 4,258,058 discloses phenoxyalkyl carboxylic acid derivatives which are thromboxane $A_2$ blocking agents. European Pat. No. 194,548A discloses sulphonamido-ethyl compounds which are useful in treating or preventing thrombembolic diseases by inhibiting thrombocyte aggregation.

DETAILED DESCRIPTION OF THE INVENTION

It has now been discovered that compounds represented by the formula wherein X is halogen, lower alkyl, arylalkyl, alkoxy, or hydroxy, wherein the phenyl ring can be mono or di-substitued; R' is —COOH, wherein R" is lower alkyl or aryl; wherein n and m are integers and can be independently zero, one, two or three are potent thromboxane $A_2$ receptor antagonists.

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl,nonyl, decyl, undecyl, dodecyl, the various branched isomers thereof, and the like as well as such groups including a halo-substituent, such as F, Br, Cl or I or $CF_3$, an alkoxy substitutent, a haloarylsubstituent, a cycloalkyl substituent (that is, cycloalkylalkyl) or an alkylcycloalkyl substituent.

The term "aryl" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl, may be lower alkyl, halogen (Cl, Br or F), or lower alkoxy.

The term "aralkyl" as used herein refers to lower alkyl groups as discussed above having an aryl substituent, such as benzyl.

The term "alkoxy" includes any of the above lower alkyl groups linked to an oxygen atom.

Preferred compounds of formula I are where m is one and n is one or two or m is two and n is one and R' is COOH and X is chloro.

The various compounds of the invention may be prepared as outlined below.

A suspension of an amine of structure II and anhydrous sodium acetate in ethanol is reacted with a solution of an aryl sulfonyl chloride in ethanol to yield a sulfonamide compound having the formula The compound of formula III and an unbranched alkanoyl chloride are dissolved in dry benzene and cooled to 0° C. Anhydrous stanic chloride is added to this solution at 0° C. and a compound having the formula is obtained. A compound of formula IV where alkyl=$CH_3$ is dissolved in a mixture of methanol and perchloric acid to which thallium (III) nitrate is added. The compound having the formula V is obtained. Hydrolysis of the methyl ester V under art recognized procedures (KOH, $H_2O$, MeOH) affords a compound of formula VI Alternatively, compounds of formula IA where R'=COOH are obtained by heating a compound of formula IV with sulfur and morpholine followed by hydrolysis with a strong base such as KOH and acidification.

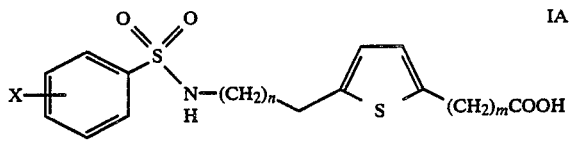

An alternative procedure to prepare compounds of structure I where m is more than 1 is as follows:

A compound of structure VI is first treated with thionyl chloride in hot benzene to yield compounds of structure VII

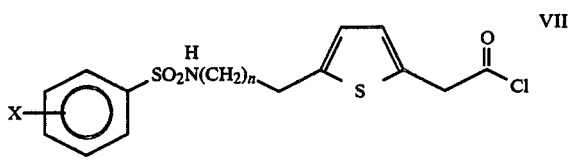

Compounds of structure VII in mixtures of inert organic solvents such as ether or tetrahydrofuran are then treated with a solution of diazomethane to yield after concentration in vacuo compounds of structure VIII.

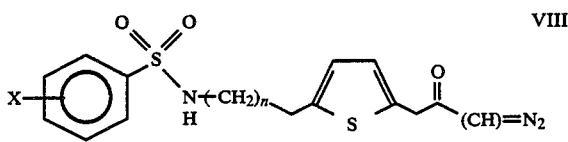

Compounds of structure VIII are then converted to compounds of structure IB by heating them in the presence of silver metal or a silver (I) salt such as silver (I) oxide in a little water to yield a compound of structure IB where R′=COOH, or an alkanol, to yield a compound of structure IB where R′=COOalkyl.

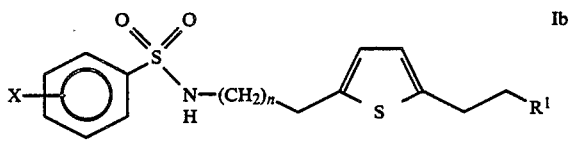

Compounds of structure Ib where R′=COOalkyl may be converted to compounds of structure I where R′=COOH by hydrolysis as described above. The process described above may be repeated sequentially to yield compounds of structure I where m is more than 2.

In the case of compounds of formula 1 where X is hydroxy the previously described procedures are applicable providing that the hydroxy group of the arylsulfonyl halide is previously protected using standard protecting groups such as

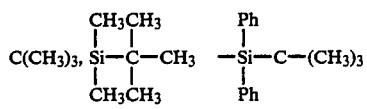

or the like. Thus a protected arylsulfonyl halide such as IX

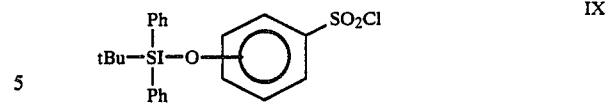

would be allowed to react with compounds of structures II as previously described to yield compound of structure X

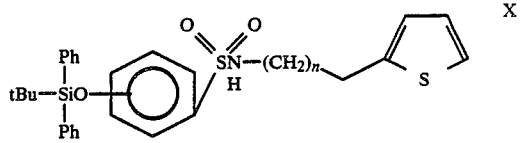

Compounds of structure X would then be transformed as previously described to compounds of structure

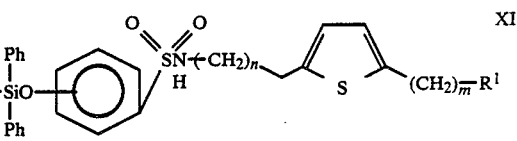

which would then be deprotected using standard chemical means to provide compounds of structure I where X=OH.

Compounds of structure I where R′=5-tetrazolyl can be prepared by converting compounds of structure I where R′=COOH to structures of formula I where R′=CN by standard chemical means and then to compounds of structure I where R′=5-tetrazolyl by treatment with an inorganic azide such as ammonium azide in an organic solvent such as dimethylformamide. Compound of structure I where R′=

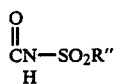

are prepared from compounds I where R′=COOH by treatment with thionyl chloride or the like in organic solvents such as benzene or tetrahydrofuran and subsequently with sulfonamides with the formula

in the presence of an organic base such as pyridine or triethylamine or in the presence of an inorganic base such as sodium bicarbonate or potassium carbonate or the like.

The compounds of this invention are cardiovascular and pulmonary agents and are useful as platelet aggregation inhibitors, such as in inhibiting arachidonic acid-induced platelet aggregation, e.g., for treatment of thrombotic disease such as coronary or cerebral thromboses, and in inhibiting bronchoconstriction. They are selective thromboxane $A_2$ receptor antagonists e.g., having a vasodilatory effect for treatment of myocardial ischemic disease, such as angina pectoris.

The compounds of this invention may also be used in combination with a cyclic AMP phosphodiesterase (PDE) inhibitor such a theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 0.1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees of Centigrade.

EXAMPLE 1

5-(2-(((4-chlorophenyl)sulfonyl)amino)ethyl)2-thiopheneacetic acid

A. N-(2-(Thien-2-yl)-ethyl)-4-chlorobenzenesulfonamide. To a suspension of 2-(thien-2-yl)ethylamine (1.118 g, 8.79 mmol) and anhydrous sodium acetate (1.44 g, 17.6 mmol) in 6 ml of 100% ethanol was added, dropwise, a solution of 4-chlorobenzenesulfonyl chloride (1.86 g, 8.79 mmol) in 20 ml of 100% ethanol. The reaction was stirred for 30 min. Three additional 100 mg portions of the sulfonyl chloride were added at 20 min. intervals to drive the reaction to completion. After an additional 5 min., the reaction was concentrated in vacuo. The residue was taken up in 5 ml of water and brought to pH 3 with 6N HCl. The mixture was extracted with three 50 ml portions of ether. The combined organic phases were dried (sodium sulfate) and concentrated in vacuo. The residue was then freed of acetic acid by adding 5 ml of toluene followed by evaporation in vacuo. The crude product, a yellow solid weighing 2.56 g (97%), was used in the next reaction:

B. N-(2-(5-Acetyl-thien-2-yl)-ethyl)-(4-chlorobenzene)sulfonamide. The product from Section A (2.36 g, 7.82 mmol) and acetyl chloride (0.67 ml, 9.38 mmol) were dissolved in dry benzene and cooled to 0° C. To the cold solution was rapidly added anhydrous tin (IV) chloride (0.92 ml, 7.82 mmol); a sticky orange/black precipitate formed which impeded stirring. The cold bath was removed and the precipitate was broken up with a spatula. The mixture was stirred for 20 min. and then quenched with 10 ml of 2N HCl. Ether (25 ml) was then added to dissolve the remaining solids. The layers were separated and the aqueous phase was extracted with two 25 ml portions of ether. The combined organic layers were washed with water and then extracted with 25 ml of 2N NaOH. An oil settled in the separatory funnel. This oil and the aqueous phase were removed and the organic phase was extracted with another 25 ml portion of 2N NaOH. The organic phase contained only some N-acylated product. Thus, the organic phase was concentrated in vacuo. The residue was dissolved in 10 ml of methanol and 4 ml of 2N NaOH was added. After standing for 10 min. the hydrolysis was complete and the mixture was concentrated in vacuo. The residue and the basic extracts obtained above were acidified to pH 1 with 6N HCl. The resultant mixture was extracted with three 40-ml portions of methylene chloride. The combined organic extracts were dried using sodium sulfate and concentrated in vacuo. The residue was dissolved in a minimum amount of methylene chloride and purified by flash chromatography (20 cm×50 mm silica, 50% ethyl acetate-hexanes) which provided a yellowish solid: 2.15 g (80%).

C. Methyl 5-(2-(((4-chlorophenyl)sulfonyl)amino)ethyl)-2-thiopheneacetate. The product from Section B (2.15 g, 6.25 mmol) was dissolved in a mixture of 90 ml of methanol and 5 ml of 70% perchloric acid to which was added thallium (III) nitrate trihydrate (3.06 g, 6.88 mmol). After stirring for 16 h, the reaction was filtered. The solids were washed with methanol and the combined filtrate and washing were concentrated in vacuo to ca. 30 ml. This mixture was diluted with 100 ml of water and extracted with three 75-portions of methylene chloride. The combined organic phases were dried (sodium sulfate) and concentrated in vacuo. The residue was purified by flash chromatography (15 cm×50 mm silica, 35% ethyl acetate-hexanes) which provided 2.14 g (91%) of a yellowish solid: mp 41°–42.5° C.;

D. 5-(2-(((4-chlorophenyl)sulfonyl)amino)ethyl)-2-thiopheneacetic acid. The product from Section C (500 mg, 1.34 mmol) was dissolved in 5 ml of methanol. To this solution was added 2 ml of 2N KOH and the transiently yellow solution was stirred for 2 hours. The mixture was concentrated in vacuo. Water (5 ml) was added to the residue. The mixture was then acidified to pH 2 with 6N HCl. The solid was collected by filtration, washed with 5 ml of water and dried in vacuo to provide 472 mg (98%) of a white solid. Recrystallization from ethyl acetate-hexanes provided 398 mg of fine white plates: mp 137.5°–138.5° C.; Anal. Calcd for $C_{14}H_{14}NO_4S_2Cl$; C, 46.73; H, 3.92; N, 3.89; S, 17.82; Cl, 9.85. Found: C, 46.71: H, 3.94; N, 3.82; S, 17.49; Cl, 9.94.

EXAMPLE 2

(5-(3-(((4-chlorophenyl)sulfonyl)amino)propylthien-2-yl)acetic acid

A. 2-(2-Bromoethyl)thiophene. To a 65° C. solution of 2-(2-thienyl)ethanol(5.0 g, 39.0 mmol) in carbon tetrachloride (100 ml) was added, carefully in one portion, phosphorus (III) bromide (4.4 ml, 46.8 mmol). After stirring for 20 minutes, the reaction was cooled to room temperature and poured onto ice (ca. 100 g). The organic layer was separated. The aqueous layer was extracted with methylene chloride (3×50 ml). The four combined organic layers were washed (50 ml of saturated (NaHCO$_3$) dried (Na$_2$SO$_4$) and concentrated in vacuo to a volume of ca. 50 ml. The residue was distilled-first at atmospheric pressure to remove solvent-then in vacuo to provide the above titled compound as a transparent water-white liquid: 3.76 g (50%);

B. 3-(thien-2-yl)propanonitrile. To a solution of the compound of Section A (3.75 g, 19.6 mmol) in 95% ethanol (20 ml) was added a solution of potassium cyanide (3.83 g, 58.9 mmol) dissolved in water (ca. 3 ml). The mixture was then refluxed for 2.5 h and then cooled. Most of the alcohol was removed in vacuo. The residue was partitioned between ether (50 ml) and an equal volume of water. The aqueous phase was extracted with ether (50 ml). The combined organic layers were dried (Na$_2$SO$_4$) and concentrated in vacuo. Distillation of the residue in vacuo yielded a transparent water-white liquid: 2.30 g (86%);

C. 3-(thien-2-yl)propylamine. Ether (50 ml) was slowly added to aluminum (III) chloride (0.972 g, 7.29 mmol) at 0° C. To this solution was added, portionwise, lithium aluminum hydride (0.277 g, 7.29 mmol). To this solution was then added, dropwise, a solution of the compound of Section B (1.0 g, 7.29 mmol) dissolved in ether (5 ml). After stirring for 10 minutes, water (10 ml) was slowly added to the reaction. The mixture was then brought to pH 10 with 19N NaOH. The layers were separated and the organic layer was extracted with ether (3×50 ml). The combined organic layers were dried ($Na_2SO_4$) and concentrated in vacuo. Bulb-to-bulb distillation yielded a transparent water-white liquid: $bp_3$ 130° C. (pot temp.); 919.5 mg (89%).

D. N-(3-(thien-2-yl)propyl)-4-chlorobenzenesulfonamide. To the amine of Section C (500 mg, 3.54 mmol) and sodium acetate (581 mg, 7.08 mmol) in 100% ethanol (15 ml) was added, dropwise, 4-chlorobenzenesulfonyl chloride (971 mg, 4.60 mmol) dissolved in ethanol (ca. 20 ml). After stirring for 20 minutes, the reaction was filtered. The solids were washed with ethanol and the combined filtrates were concentrated in vacuo. The residue was diluted with water (15 ml) and brought to pH 10 with 2N NaOH. The solution was extracted with methylene chloride (2×30 ml). The combined organic layers were dried ($Na_2SO_4$) and concentrated in vacuo to provide a solid: 1.10 g (98%).

E. N-(3-(5-acetyl-thien-2-yl)propyl)-4-chlorobenzenesulfonamide. To a 0° C. mechanically stirred solution of the preceding sulfonamide of Section D and acetyl chloride (0.322 ml, 4.53 mmol) in benzene (10 ml) was added tin (IV) chloride (0.428 ml, 3.66 mmol) in one portion. The reaction, now containing an orange precipitate, was allowed to warm to room temperature. An additional portion of acetyl chloride (0.322 ml. 4.53 mmol) was then added. After 20 minutes, the blue reaction was quenched with water (15 ml). After all the solids had dissolved, the layers were separated. The aqueous layer was extracted with methylene chloride (2×25 ml). The combined organic layers were dried ($Na_2SO_4$) and concentrated in vacuo. The residue was dissolved in methanol (10 ml) to which was then added 0.25M potassium carbonate in 4/1 methanol/water (3 ml). After 30 minutes, the reaction was concentrated in vacuo. The residue was acidified with 1N HCl to ca. pH 1 and extracted with methylene chloride (3×20 ml). The combined organic layers were dried ($Na_2SO_4$) and concentrated in vacuo. After this base hydrolysis, TLC indicates absence of N-acylated product (Rf 0.09, silica, 25% ethyl acetate-hexanes). For the product: 1.21 g (97%).

F. Methyl (5-(3-(((4-chlorophenyl)sulfonyl)amino)propyl)thien-2-yl)acetate. The preceding ketone of Section E (ca 3.38 mmol) was dissolved in methanol (10 ml). To this solution were added, sequentially, perchloric acid (70%, 1.7 ml) and thallium (III) nitrate trihydrate (1.80 g, 4.06 mmol). After stirring for 21 hours, the reaction was filtered and the solids were washed with methanol. The combined filtrates were poured into water (20 ml) and extracted with methylene chloride (4×20 ml). The combined organic layers were dried ($Na_2SO_4$) and concentrated in vacuo to a brown oil. Chromatography (flash, silica, 37 mm×15 cm, 40% ethyl acetate-hexanes) provided a colorless solid: 760 mg (58%).

G. (5-(3-(((4-chlorophenyl)sulfonyl)amino)propyl)-thieny-2-yl)acetic acid, The preceding ester of Section F (760 mg, 1.96 mmol) was dissolved in methanol (20 ml). To the solution was added 2N KOH (6 ml). After standing for 1.5 hours, the methanol was removed in vacuo. To the residue was added water (20 ml) and then 1N HCl to bring the pH to 1.5. The precipitated solid was collected by filtration, washed with water and air dried. Recrystallization from ethyl acetatehexanes provided white crystals: 565 mg (77%); mp 134.5°-135° C. Anal. calcd for $C_{15}H_{16}ClNO_4S_2$: C, 48.19; H, 4.31; N, 3.75; Cl, 9.48; S, 17.15. Found: C, 48.03; H, 4.35; N. 3.73; Cl, 9.89; S, 17.30.

EXAMPLE 3

3-(5-(2-(((4-chlorophenyl)sulfonyl)amino)ethyl)thien-2-yl)propionic acid

A. Methyl 3-(5-(2-(((4-chlorophenyl)sulfonyl)amino)ethyl)thien-2-yl)propionate. A solution of the title compound of Example 2 (500 mg, 1.40 mmol) in ca. 1 ml of thionyl chloride was heated at reflux for 20 minutes. The excess thionyl chloride was then removed by distillation at slightly reduced pressure. Then, benzene (4 ml) was added to the pot and subsequently distilled to remove traces of thionyl chloride. The residue was dried in vacuo. The resultant solid was dissolved in ether (ca. 5 ml) containing a little THF. This solution was added dropwise to ethereal diazomethane (ca. 12 ml of ca 0.3M) at 0° C. An additional 6 ml of diazomethane solution was when added to complete formation of the diazoketone. After 5 minutes, the solvent was removed in vacuo. The residue was taken up in methanol (20 ml) and warmed to 60° C. Portions of silver (1) oxide (ca. 40 mg each) were added to the hot solution at 15 minute intervals. After 1.5 hours, the mixture was treated with Norit and filtered through Celite. The filtrate was concentrated in vacuo. The residue was then taken up in methylene chloride and passed through a short plug of silica eluting with 1:1 methylene chloride/ethyl acetate. The eluate was concentrated in vacuo to 399 mg of a solid. This material was combined with a material from a previous reaction (126 mg) and chromatographed (flash, silica, 25×15 cm, 40% ethyl acetate-hexanes) to provide 357 mg (47% yield) of a white solid.

B. 3-(5-(2-(((4-chlorophenyl)sulfonyl)amino)ethyl)-thien-2-yl)propionic acid. The preceding ester of Section A was hydrolyzed by dissolving it in methanol (ca 10 ml) and stirring with 2N KOH (2 ml) for 1.5 hours. After this time, the reaction was concentrated in vacuo. The residue was acidified to pH 2 with 1N HCl. The precipitated solid was collected by filtration, washed with water and air dried. Recrystallization from ethyl acetate-hexanes provided a crop of yellow crystals. A second crop (33 mg, 10% yield, mp 127°-129.5° C.) was obtained from the mother liquors. For the first crop: 257.3 mg (75% yield); mp 131°-132° C. Anal. calcd for $C_{15}H_{16}ClNO_4S_2$: C, 48.19; H, 4.31; N, 3.75; Cl, 9.48; S, 17.15. Found: C, 48.25; H, 4.26; N, 3.67; Cl, 9.63; S, 16.85.

What is claimed is:

1. Compounds represented by the formula

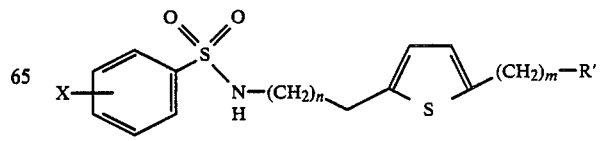

wherein X is halogen, lower alkyl, arylalkyl, alkoxy or hydroxy; wherein the phenyl ring is mono or di-substituted, R' is —COOH or

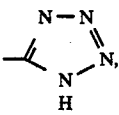

or

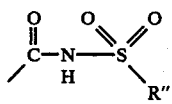

wherein R" is lower alkyl or aryl and n and m are independently zero, one, two or three.

2. A compound according to claim 1 wherein n and m are one.

3. A compound according to claim 1 wherein m=1 and n=2.

4. A compound according to claim 1, wherein m=2 and n=1.

5. A compound according to claim 1 wherein R' is —COOH.

6. A compound according to claim 1, 5-(2-(((4-chlorophenyl)sulfonyl)amino)ethyl)-2-thiopheneacetic acid.

7. A compound according to claim 1 3-(5-(2-(((4-chlorophenyl)sulfonyl)amino)ethyl)thien-2-yl)propionic acid.

8. A compound according to claim 1 (5-(3-(((4-chlorophenyl)sulfonyl)amino)propyl)thien-2-yl)acetic acid.

9. A method of inhibiting arachidonic acid-induced platelet aggregation and bronchoconstriction which comprises administering to the circulatory system of a mammalian host an effective amount of a compound as defined in claim 1 or a pharmaceutically acceptable salt thereof.

10. The method as defined in claim 8 wherein said compound is administered in an amount within the range of from about 0.1 to about 100 mg/kg.

11. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

12. A method of inhibiting platelet aggregation which comprises administering to a mammalian host an effective amount of a compound as defined in claim 1 or a pharmaceutically acceptable salt thereof.

13. A method of inhibiting bronchoconstriction associated with asthma, which comprises administering to a mammalian host an effective amount of a compound as defined in claim 1 or a pharmaceutically acceptable salt thereof.

14. A method of treating peripheral vascular diseases, which comprises topically or systemically administering to a mammalian host an effective amount of a compound as defined in claim 1 or a pharmaceutically acceptable salt thereof.

* * * * *